(12) United States Patent
Taylor et al.

(10) Patent No.: US 6,602,525 B1
(45) Date of Patent: Aug. 5, 2003

(54) COMPOSITIONS COMPRISING NITROFURANTOIN AND UVA URSI

(75) Inventors: Kevin Douglas Taylor, Mason, OH (US); Duane Larry Charbonneau, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/323,440

(22) Filed: Dec. 18, 2002

Related U.S. Application Data

(62) Division of application No. 10/139,839, filed on May 7, 2002, now Pat. No. 6,521,270.
(60) Provisional application No. 60/297,274, filed on Jun. 11, 2001.

(51) Int. Cl.[7] ................................................. A61K 35/78
(52) U.S. Cl. ....................................... 424/725; 514/579
(58) Field of Search ........................... 424/725; 514/579

(56) References Cited

U.S. PATENT DOCUMENTS 5,880,108 A * 3/1999 Morales et al.
5,925,377 A * 7/1999 Gerth et al.

OTHER PUBLICATIONS

Uva Ursi website (www.transgenica.com/database/u/uvaursi.htm) (1999).*

* cited by examiner

Primary Examiner—Leon B. Lankford, Jr.
Assistant Examiner—Susan D Coe
(74) Attorney, Agent, or Firm—David V. Upite

(57) ABSTRACT

Compositions and kits comprising nitrofurantoin and uva ursi are effective for treating infectious disorders, particularly urinary tract infections, cystitis, and pyelonephritis.

20 Claims, No Drawings

COMPOSITIONS COMPRISING NITROFURANTOIN AND UVA URSI

CROSS REFERENCE TO RELATED APPLICATIONS

This application is a divisional application of application Ser. No. 10/139,839 filed on May 7, 2002, now U.S. Pat. No. 6,521,270 allowed on Oct. 22, 2002, which claims priority under Title 35, United States Code 119(e) from Provisional application Ser. No. 60/297,274, filed Jun. 11, 2001, now U.S. Pat. No. 6,521,270 issued Feb. 18, 2003.

TECHNICAL FIELD

The present invention relates to compositions and kits useful in treating infectious disorders.

BACKGROUND

Urinary tract infections (UTI) are a serious health problem affecting millions of people each year. UTI infections account for about 10 million doctor visits in the United States alone, with only respiratory infections occurring more often. Many remedies are taught for the treatment of UTI.

In particular, nitrofurantoin is a well-known antibacterial compound and has been used extensively as an active ingredient in antibacterial pharmaceutical compositions. Nitrofurantoin has been used successfully for many years for the treatment of UTI. Its presumed mode of action is based upon its interference with several bacterial enzyme systems. However, the development of antibiotic resistant strains of microbes continues to be problematic, thereby diminishing the effectiveness of many antibiotics.

Herbal remedies have also been used for the treatment of UTI. In particular, *Arctostaphylos uva-ursi*, also known as bearberry, has been used as a urinary antiseptic. Indeed, teas and extracts of the leaves have been used as urinary tract antiseptic for centuries. The leaves of uva ursi contain hydroquinone derivates, mainly arbutin and methyl-arbutin. Upon consumption, arbutin is hydrolyzed in gastric fluid to hydroquinone. In alkaline urine, hydroquinone is mildly astringent and is an effective antimicrobial agent. It has been suggested that arbutin itself may contribute to the antiseptic activity of uva ursi. Despite this activity, in practice, large amounts of uva ursi must be consumed for any significant effect to occur and the urine must be alkalinized.

For the foregoing reasons, there is a continuing need to find more effective ways to treat UTI. Furthermore, there is a continuing need to find more effective ways to enhance the efficacy of existing antimicrobial compounds such as nitrofurantoin against UTI-causing microbes, particularly those resistant strains.

SUMMARY OF THE INVENTION

The present invention provides a composition comprising a safe and effective amount of nitrofurantoin and uva ursi. The invention further provides for a kit comprising (a) nitrofurantoin in a unit dose form; (b) uva ursi in a unit dose form; and (c) a package containing components (a) and (b). The administration of a composition or a unit dose form of a kit of the present invention to a subject in need thereof, is effective for the prevention and treatment of infectious disorders such as UTI, acute cystitis, and pyelonephritis. The invention is also effective for treating upper-gastrointestinal disorders.

All documents cited are, in relevant part, incorporated herein by reference; the citation of any document is not to be construed as an admission that it is prior art with respect to the present invention.

DETAILED DESCRIPTION OF THE INVENTION

I. Compositions and Kits

In accordance with the present invention, an antimicrobial composition and kit containing nitrofurantoin can achieve a higher efficacy of antimicrobial activity if complemented by uva ursi.

Furthermore, the composition and kit comprising nitrofurantoin and uva ursi according to the present invention may exhibit synergism by lowering the MIC (minimum inhibitory concentration) and even FIC (fractional inhibitory concentration) of nitrofurantoin.

The compositions of the present invention comprise: (a) a safe and effective amount of nitrofurantoin; (b) a safe and effective amount of uva ursi; and (c) optionally, a pharmaceutically-acceptable carrier.

The kits of the present invention comprise: (a) nitrofurantoin in a unit dose form; (b) uva ursi in a unit dose form; and (c) a package containing components (a) and (b). In one mode, the kit of the present invention contains nitrofurantoin and uva ursi in a single unit dose form. In another mode, nitrofurantoin and uva ursi are in separate unit dose forms. In either instance, a plurality of doses can be present to provide prevention or treatment over a period of several days, or weeks. Still another mode, instructions to the kit are included.

As used herein, "nitrofurantoin" includes the compound N-(5-nitro-2-furfurylidene)-1-aminohydantoin, as well as its pharmaceutically acceptable salts, hydrates, and complexes. (See "6696. Nitrofurantoin", The Merck Index, 12th ed. (1996, pp. 1134). Nitrofurantoin "complexes" refer to chemical complexes of nitrofurantoin with other chemical constituents that result in entities that retain at least a substantial portion of the antimicrobial activity of nitrofurantoin. Examples of such complexes include nitrofurantoin-phthaloyl glycine and nitrofurantoin-phthaloyl aminocaproic acid. A method for preparing nitrofurantoin is disclosed in U.S. Pat. No. 2,610181, to Hayes, issued Sep. 9, 1952. A method for preparing macrocrystalline nitrofurantoin is disclosed in U.S. Pat. No. 3,401,221, to Brogmann et al., issued Sep. 10, 1968. See also, U.S. Pat. Nos. 2,898,335; 2,927,110; 3,007,846; and 3,446,802 to Michels; Gever & O'Keefe; Gever & Vincent; and Michels issued Aug. 4, 1959; Mar. 1, 1960; Nov. 7, 1961; and May 27, 1969 respectively.

"Uva ursi" is a plant, including plant parts such as leaves, stems, berries roots, flowers and the like, or an extract thereof of *Arctostaphylos uva-ursi*, and related members of its family Ericaceae including, but not limited to, Vaccinium, Arctostaphylos, Gaultheria, and Gaylussacia. Preferred species include, *Arctostaphylos adenotricha*, and *Arciostaphylos coacrylis*, and *Arctostaphylos uva-ursi* most preferably *Arctostaphylos uva-ursi*. Mixtures of Ericaceae plants and /or extracts may also be used. Other names of *A. uva-ursi* include: beargrape, kinnikinnick, mealberry, mountain box, mountain cranberry, redberry leaves, sagackhomi, sandberry, hogberry, manzanita and bearberry.

A well-known homeopathic treatment for acute cystitis has been the use of uva ursi. It has now been found through in vitro microbiological testing that a combination of nitrofurantoin and uva ursi (hereinafter referred to as "the combination") results in a significant reduction in the minimal inhibitory concentration (MIC) required to inhibit the growth of certain urinary tract pathogens (see "IV. Data"). Specifically, when the combination is tested against Pseudomonas, Porteus, Serratia, and Klebsiella there was a significant decrease in the MIC values for nitrofurantoin. Historically, all of these pathogens are known to be moderately or highly resistant to nitrofurantoin. Additionally, there is synergistic activity seen against Serratia as evidenced by the concurrent lowering of MIC for uva ursi. Together these results suggest that the combination may be beneficial in the treatment of infectious disorders such as acute cystitis caused by pathogens not adequately eradicated by either nitrofurantoin or uva ursi alone.

As discussed above, the combination is effective for treating and preventing infectious disorders. Thus, the combination can be formulated into pharmaceutical compositions or packaged as a kit. Standard pharmaceutical formulation techniques are used, such as those disclosed in *Remington's Pharmaceutical Sciences*, Mack Publishing Company, Easton, Pa., latest edition.

A "safe and effective amount" of nitrofurantoin and uva ursi is an amount, taken concurrently, that is effective to treat an infectious disorder in an animal, preferably a mammal, more preferably a canine, feline, or human, still more preferably a human subject, without undue adverse effects (such as toxicity, irritation, or allergic response), commensurate with a reasonable benefit/risk ratio when used in the manner of the present invention. The term "concurrently," as used herein, means that uva ursi and nitrofurantoin are administered within 24 hours of each other, preferably conjointly. The specific "safe and effective amount" will, obviously, vary with such factors as the particular infectious disorder being treated, the physical condition of the patient, the duration of treatment, the nature of concurrent therapy (if any), the specific dosage form to be used, the carrier employed, the solubility of dose form, and the particular dosage regimen.

In addition to the safe and effective amounts of the combination, the compositions of the present invention optionally contain a pharmaceutically-acceptable carrier. The term "pharmaceutically-acceptable carrier," as used herein, means one or more compatible solid or liquid filler diluents or encapsulating substances which are suitable or administration to an animal, preferably a mammal, more preferably a canine, feline, or human, still more preferably a human. The term "compatible," as used herein, means that the components of the composition are capable of being commingled with nitrofurantoin and uva ursi, and with each other, in a manner such that there is no interaction that would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a feline, canine, and human, even more preferably a human being treated.

Some examples of substances which can serve as pharmaceutically-acceptable carriers or components thereof are: sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the combination is basically determined by the way the composition is to be administered.

If the subject composition is to be injected, the preferred pharmaceutically-acceptable carrier is sterile, physiological saline, with a blood-compatible colloidal suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers. isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions and kits of the present invention are preferably provided in unit dosage form. As used herein, a "unit dosage form" is an amount of the combination that is suitable for administration concurrently to an animal, preferably a mammal, more preferably a canine, feline, or human, still more preferably a human subject, in a single dose, according to good medical practice. These unit dosage forms preferably contain from about 1 mg (milligram) to about 10,0000 mg, more preferably from about 10 mg to about 3,000 mg, more preferably from about 20 mg to about 2,000 mg of the combination. In an embodiment of a kit of the present invention where nitrofurantoin and uva ursi are in separate unit dose forms, the two separate unit dose forms cumulatively contain the combination in the above-identified ranges.

The compositions of the present invention may be in any of a variety of forms, suitable, for example, for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the antimicrobial activity of the combination. The amount of carrier employed in conjunction with the combination is sufficient to provide a practical quantity of material for administration per unit dose of the combination. Techniques and compositions for making dosage forms useful in the methods of the present invention are described in the following references: *Modern Pharmaceutics*, Chapters 9 and 10 (Banker & Rhodes, editors, 1979); Lieberman et al., *Phannaceutical Dosage Forms: Tablets* (1981); and Ansel, *Introduction to Pharnaceutical Dosage Forms* $2^{nd}$ Edition (1976).

Various oral dosage forms can be used, including such solid forms as tablets, capsules, granules and bulk powders. These oral forms comprise a safe and effective amount, usually at least about 5%, preferably from about 10% to about 95%, and more preferably from about 25% to about 50% by weight, of the combination. Typical ratios ranges of uva ursi to nitrofurantoin are about 1:2 to about 1:100, preferably about 1:5 to about 1:40. Tablets can be compressed, tablet triturates, enteric-coated, sugar-coated, film-coated, or multiple-compressed. containing suitable binders, lubricants, diluents, disintegrating agents, coloring agents, flavoring agents, flow-inducing agents, and melting agents. One form of tableting technology that may be applicable to the present invention, particularly a unit form of uva ursi, is a liquid/liquid extract developed by Janssen Pharmaceutica Inc. and is identified by the trade name Quicksolv®. This technology is fully described in U.S. Pat. No. 5,215,756, to Gole et al., issued Jun. 1, 1993. Liquid oral dosage forms include aqueous solutions, emulsions, suspensions, solutions and/or suspensions reconstituted from non-effervescent granules, and effervescent preparations reconstituted from effervescent granules, and containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability which are not critical for the purposes of the present invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-pendent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Alternatively, the compositions of the present invention may be achieved by incorporating unit dose forms of the combination into freeze-dried or lyophilized tablets. Freeze-drying or lyophilization facilitates disintegration of the composition by rapid permeation by the aqueous media, promoting timely delivery of the produce. Suitable methods of freeze-drying are well known in the art and commonly employed. Any suitable conventional method of freeze-drying may be utilized. A preferable method of freezing and drying is to fast freeze the composition and then dry the composition to a final moisture content of about 2% to about 5%. Suitable methods of freeze-drying and production are taught by U.S. Pat. No. 4,642,903, Feb. 17, 1987, to Davies, U.S. Pat. No. 4,946,684, Aug. 7, 1990, to Blank et al., U.S. Pat. Nos. 4,305,502 and 4,371,516, issued Dec. 15, 1981 and Feb. 1, 1983 respectively, to Gregory et al., and U.S. Pat. No. 5,188,825, Feb. 23, 1993, to Iles et al.

Similarly, unit dose forms of the combination may be vacuum dried. Vacuum drying involves at least the partial drying of compositions at temperatures above compositions' collapse temperature. Freeze drying, on the other hand, involves the drying of composition at temperatures below the composition's collapse temperature. Any suitable method of vacuum drying may be used. Suitable vacuum drying processes are described in U.S. Pat. No. 5,298,261, to Pebley et al., issued Mar. 29, 1994.

Other compositions useful for attaining systemic delivery of the combination include topical (e.g., transdermal "patch"), sublingual, buccal, suppository, and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The pH of the compositions of the present invention may be adjusted by addition of a pharmaceutically-acceptable acid or base. Suitable acids include, for example, hydrochloric acid and carboxylic acids such as citric acid, tartaric acid and succinic acid. Suitable bases include, for example, the oxides and hydroxides of calcium, potassium, sodium and magnesium, alkaline quanternary compounds, alkaline amino acids, and mixtures thereof. The compositions of the present invention are preferably pH balanced and/or buffered between about 5 to about 8.

The compositions of the present invention may optionally include additional antimicrobial agents. Non-limiting examples include: sulfa drugs (sulfonamides), amoxicillin, cephalosporins, trimethoprim-sulfamethoxazole, and doxycycline.

The compositions of the present invention may optionally include other drug actives. For example, analgesics may also be included such as acetaminophen, acetyl salicylic acid, indomethacin and optically active isomers or racemates of ibuprofen, naproxen, flurbiprofen, carpofen, tiprofenic acid, cicloprofen, ketoprofen, ketorolac, etodolac, indomethacin, sulindac, fenoprofen, diclofenac, piroxicam, benzydomine, nabumetone, their pharmaceutically acceptable salts and mixtures thereof. Another example, gastrointestinal agents may also be included such as anticholinergics including atropine, clidinium and dicyclomine; antacids including aluminum hydroxide, bismuth subsalicylate, bismuth subcitrate, simethicone, calcium carbonate and magaldrate; $H_2$-receptor antagonists including cimetidine, famotidine, nizatidine and ranitidine; laxatives including: docusate. phenolphthalein and casanthrol; gastroprotectants including sucralfate and sucralate humidgel; gastrokinetic agents including metoclopramide and cisapride; proton pump inhibitors including omeprazole and antidiarrheals including: diphenoxylate, kaolin pectin, attapulgite and loperamide.

The compositions the present invention may optionally include additional plant extracts. Such plants or extracts include Echinacea, allium, bucha, juniper, ginseng, allicin, chlorella, algin, plants under the Ericaceae family, asparagus, birch, couch grass, goldenrod, horsetail, java tea, lovage, parsley, spiny restharrow, and the like.

The compositions of the present invention may optionally include nutritional supplements such as bromelain, vitamin A, and vitamin C.

As previously stated, in one mode, the unit dose forms of nitrofurantoin and uva ursi of the kits of the present invention are in separate unit dose forms. Non-limiting examples of nitrofurantoin in a separate unit dose form include: nitrofurantoin crystals per U.S. Pat. No. 5,332,832, to Cazer et al., issued Jul. 26, 1994; liquid suspensions of nitrofurantoin per U.S. Pat. No. 5,178,880, to Shahi et al., issued Jan. 12, 1993; dual-action tablet as illustrated in U.S. Pat. No. 5,032,406, to Dansereau & Kane, issued Jul. 16, 1991; nitrofurantoin dosage form per U.S. Pat. No. 4,772,473, to Patel et al., issued Sep. 20, 1988; and nitrofurantoin sustained release tablet per U.S. Pat. No. 4,122,157, to Huber, issued Oct. 24, 1978. A preferred unit dose form of nitrofurantoin is Macrobid® as exemplified in U.S. Pat. No. 4,772,473.

Non-limiting examples of uva ursi in a separate unit dose form include whole plant, including leaves (preferably), stems, shoots, berries, roots, and flowering parts, these can be ground, shredded or otherwise macerated and reduced in size for convenient use, and extracts thereof, as well as those unit dose forms commercially available including extracts, powders, capsules, gel caps, tablets, liquid, suspension, and tincture forms. Extracts can include both aqueous and organic solvent extract, e.g. ethanol, if desired, the extract can be dried and the resulting dried extract employed herein. For example, uva ursi leaf and uva ursi extract are available from Gaia Herbs, Inc. in Brevard, N.C. and Nature's Answer®, Springville, Utah; Green Kingdon Herbs. Bay City, Mich. Also encompassed are those commercially available products that contain at least some uva ursi in part. For example, many teas contain uva ursi such as Gerard House Herbal powder No. 8®, Potter's Kas-bah Herb®; Potter's Sciargo Herb®, and Wellwoman Herbs®. Also further encompassed are capsules and tablets containing uva ursi marketed for remedies such as for backaches and rheumatic pain. An example is Melfade®, by Pentapharm Ltd, Basel Switzerland.

II. Methods of Administration.

The compositions and unit dose form of kits of the present invention can be administered to treat infectious disorders in a subject in need thereof. As used herein, an "infectious disorder" is any disorder characterized by the presence of a microbial infection. Preferred methods of the present invention are the treatment of bacterial infections, particularly genitourinary infections, and gastrointestinal infections. Included within infectious disorders are generalized UTI, acute cystitis, and pyelonephritis. Included within bacterial infections are those infections caused by *Pseudomonas aeruginosa, Serratia marcescens, Enterococcus Faecalis, Klebsiella pneumoniae, Porieus mirabilis, Escherichia coli,* and/or *Staphylococcus saprophyticus.*

One skilled in the art would readily identify an infectious disorder. For example, the diagnostic techniques for a ULI include, but are not limited to, palpation over the kidney urinalysis, urine culture (clean catch), urine culture (catheterized specimen), blood culture, intravenous pyelogram scan, computed tomography scan, voiding cystourethrogram, renal ultrasound, renal scan, and renal biopsy.

Symptoms of infectious disorder are readily identifiable by those skilled in the art. For example, the symptoms of UTI include, but are not limited to, pressure in the lower pelvis, painful urination (dysuria), frequent need to urinate, urgent need to urinate, need to urinate at night, cloudy urine, blood in the urine (hematuria), and foul or strong urine odor.

The term "treatment" is used herein to mean that, at a minimum, administration of a compound or kit of the present invention mitigates an infectious disorder in a mammalian subject, preferably in humans. Thus, the term "treatment" includes: preventing an infectious disorder from occurring in a mammal, particularly when the mammal is predisposed to acquiring the infectious disorder, but has not yet been diagnosed with the disease, inhibiting the infectious disorder; and/or alleviating or reversing the infectious disorder. Insofar as the methods of the present invention are directed to preventing an infectious disorder, it is understood that the term "prevent" does not require that the infectious disorder be completely thwarted. (See Webster's Ninth Collegiate Dictionary.) Rather, as used herein, the term "preventing" refers to the ability of the skilled artisan to identify a population that is susceptible to infectious disorders, such that administration of the compounds and kits of the present invention may occur prior to the onset of the symptoms of the infectious disorder. The population that is at risk for an infectious disorder, particularly an UTI, include those who are subjected to: an obstruction of the bladder or urethra with resultant stasis of urine, insertion of instruments into the urinary tract (such as cateterization or cystoscopy), pregnancy, diabetes, and a history of analgesic nephropathy or reflux nephropathy. The elderly population is at increased risk for developing an UTI due to lack of mobility and/or incomplete emptying of the bladder associated with such conditions are benign prostatic hyperplasia, prostatitis, and urethral strictures.

Thus, the patient population is identifiable and could receive the administration of a composition or unit dose form of a kit of the present invention before progression of the disease. Thus, progression of the infectious disorder in such individuals would be "prevented."

The compositions and kits of the present invention are also useful for prophylactic or acute treatment. The compositions and dose form of kits of the present invention are administered in any way the skilled artisan in the field of medicine or pharmacology would desire. It is immediately apparent to the skilled artisan that preferred routes of administration depend on the infectious disorder being treated and the dosage form chosen. A preferred route for systemic administration includes perorally.

The preferred methods of the present invention also include methods for the treatment and prophylaxis of upper-gastrointestinal disorders mediated by *Campylobacter pylori*. For example, the compositions and unit dose form of kits of the present invention can be used for the prevention and treatment of *C. pylori* mediated ulcers. Such methods and others are generally described in European Patent Publication 219,912, Kraft et al. published Apr. 29, 1987.

The compositions and unit dose form of kits of the present invention can be administered systemically. Systemic application includes any method of introducing a composition or unit dose form of a kit of the present invention into the tissues of the body, for example, epidural, intramuscular, transdermal, intravenous, intraperitoneal, subcutaneous, sublingual, rectal, and oral administration. The compositions and unit dose form of kits of the present invention are preferably administered orally.

The specific dose of a composition or unit dose form of a kit of the present invention to be administered, as well as the duration of treatment, are mutually dependent. The dosage and treatment regimen will also depend upon such factors as the route of administration, the type of dosage form used, the infectious agent present, the ability of the combination to reach and sustain effective levels at the site of infection, the nature and extent of other infections (if any), the personal attributes of the subject (such as weight), compliance with the treatment regimen, and the presence and severity of any side effects of the treatment.

For systemic administration of the compositions or unit dose form of kits, typically for a human adult (weighing approximately 70 kilograms), from about 1 mg to about 10,000 mg, preferably from about 10 mg to about 5000 mg of the compositions or unit dose form of kits are administered per day.

Treatment regimens preferably extend from about once to about five times daily, for about 1 to about 56 days, preferably for about 3 to about 10 days, It is understood that these dosage ranges are by way of example only, and that daily administration can be adjusted depending on the factors listed above.

III. Data

A. Introduction

Antimicrobial combinations are sometimes used to provide broad-spectrum treatment. Combinations of antimicrobial agents may be chosen because a pathogen is resistant to inhibition and/or killing by conventional doses of a siraje agent but susceptible to the same agent in combination with another agent. Nitrofurantoin has broad-spectrum activity against Gram-positive and Gram-negative bacteria. Particularly the common UTI pathogens. In particular, nitrofurantoin is active against Gram-positive cocci such as *Staphylococcus aureus, Staphylococcus epidermidis, Staphylococcus saprophyticus* and *Enterococcus faecalis*. Over 90% of *Escherichia coli* and many coliform bacteria are susceptible. However, only ⅓ of Enterobacter and Klebsiella isolates are susceptible. Pseudomonas and most Proteus species are resistant.

The present study evaluated combination therapy with nitrofurantoin and uva ursi (specifically, *Arctostaphylos uva-ursi*) extract and determined the effectiveness of such a combination approach. The study also evaluated if there was synergism between nitrofurantoin and uva ursi. "Synergism" is a positive interaction between two drugs; the combined effect of the drugs being examined is greater than the expected results based on their independent effects when the drugs are used separately. Synergism should be distinguished from "additivity," which is defined, as the effect of two drugs used together is equal to the sum of the effects of each drug used separately. "Antagonism" is the effect of two drugs used together is less than the sum of the effects of each drug used separately.

The checkerboard (or chessboard) method is used to assess the antimicrobial combination in vitro against the following selection of Gram-positive and Gram-negative pathogens including: *Escherichia coli, Klebsiella pneumoniae*, Proteus mirabilis, *Serratia marcescens, Staphylococcus saprophyticus, Pseudomonas aeruginosa*, and *Enterococcus faecalis*. It was found that the combination of nitrofurantoin with uva ursi is capable of reducing the MIC of nitrofurantoin again nearly all isolates tested. Furthermore, the combination of nitrofurantoin and uva ursi is synergistic against four of the seven species tested, in particular *E. coli, S. marcescens, P. mirabilis*, and *P. aeruginosa*.

Without being limited by theory, it is believed that, the synergy between nitrofurantoin and uva ursi is actually between nitrofurantoin and either arbutin, methyl-arbutin and/or hydroquinone. This is surprising in light of the antagonism that has been reported between nitrofurantoin and other antibiotics such as reported in Shah, S. & D. Greenwood, "Interactions between antibacterial agents of the quinolone group and nitrofurantoin," *Journal of Antimicrobial Chemotherapy*, Vol. 21, pp. 41–48 (1998).

B. Materials and Methods

Utilizing the checkerboard (or chessboard) method, concentrations of nitrofurantoin monohydrate (0.5–256 $\mu$g/mL) and uva ursi (specifically, *Arctostaphylos uva-ursi*) extract (0.125–8 $\mu$g/mL in 40% (v/v) ethanol) used ranged from four to five dilutions below the pre-test MIC for each drug to two dilutions above the pre-test MIC for each drug.

The MIC was determined for each isolate for both nitrofurantoin and the uva ursi prior to the checkerboard testing; using approved standard National Committee for Clinical Laboratory Standards (hereinafter "NCCLS") methods for microbroth dilution. *Methods for Dilution Antimicrobial Susceptibility Tests for Bacteria That Grow Aerobically; Approved Standard* (Fifth Edition) (2000). These standards are as follows:

| Organism (10 isolates each thereof) | Inoculum Preparation | Final Inoculum Size | Test Medium | Incubation Conditions |
|---|---|---|---|---|
| P aeruginosa S. marcescens E. faecalis K. pneumoniae P. mirabilis E. coli S. saprophyticus | Colonies taken from overnight growth on 5% sheep blood agar and suspended to a 0.5 McFarland Standard | 1 × 10⁶ CFU/ml | Cation-adjusted Mueller-Hinton Broth | 35° C., 18–24 hours |

Nitrofurantoin was added to cation-adjusted Mueller-Hinton Broth (hereinafter "CAMHB") and dissolved. Serial doubling dilutions were performed in CAMHB providing concentrations ranging from 0.5 $\mu$g/ml to 256 $\mu$g/ml.

The uva ursi extract was serially diluted in water. For each test concentration, the final dilution was performed in CAMHB providing dilutions of 1:20 to 1:2048.

Synergy panels were designed for each isolate based on pre-test MICs for both nitrofurantoin and uva ursi extract. Following testing, the FIC index was calculated for each isolate panel to determine whether synergy, additivity, or antagonism occurred.

$$\frac{(A)}{(MIC_A)} + \frac{(B)}{(MIC_B)} = FIC_A + FIC_B = FIC\ Index$$

wherein: (A) is the concentration of drug A in a well that is the lowest inhibitory concentration in its row; ($MIC_A$) is the MIC of the organism to drug A alone; and B) and ($MIC_B$) are defined in the same way for drug B.

For synergy, the FIC index is 0.5. For additivity, the FIC index is 1. For antagonism, the FIC index is 2.

The NCCLS reference strain for *E. coli*, ATCC 25922, was used for quality control with a MIC range of 4–16 $\mu$g/ml. There are no NCCLS reference strains for nitrofurantoin for the remaining test organisms.

C. Results a. *Pseudomonas aeruginosa*.

Pre-test MIC were all >512 $\mu$g/ml for nitrofurantoin and ranged from dilutions of 1:80 to 1:160 for uva ursi. In the presence of uva ursi, nitrofurantoin MIC ranged from 0.25→512 µg/ml. One out of ten isolates demonstrated synergy, four demonstrated additivity, and five showed no effect with the uva ursi and nitrofurantoin combinations.

TABLE 1-1

Pre test MIC of nitrofurantoin and *uva ursi* among *P. aeruginosa.*

| Isolate ID | Nitrofurantoin MIC (µg/ml) | Dilution ratio *uva ursi* |
| --- | --- | --- |
| 1 | >512 | 1:80 |
| 2 | >512 | 1:80 |
| 3 | >512 | 1:80 |
| 4 | >512 | 1:80 |
| 5 | >512 | 1:80 |
| 6 | >512 | 1:80 |
| 7 | >512 | 1:80 |
| 8 | >512 | 1:80 |
| 9 | >512 | 1:80 |
| 10 | >512 | 1:160 |

TABLE 1-2

Test results for *P. aeruginosa* showing lowest fractional inhibitory concentration

| Isolate ID | MIC (µg/ml) Nitrofuran-toin | Dilution ratio *uva ursi* | MIC for combina-tion* | *Uva ursi* Dilution ratio at MIC | Result |
| --- | --- | --- | --- | --- | --- |
| 1 | >512 | 1:80 | 256 | 1:160 | Additivity |
| 2 | >512 | 1:160 | >512 | 1:80 | NE‡ |
| 3 | >512 | 1:80 | >512 | 1:80 | NE |
| 4 | >512 | 1:80 | >512 | 1:80 | NE |
| 5 | >512 | 1:40 | 0.25 | 1:80 | Synergy |
| 6 | >512 | 1:80 | >512 | 1:80 | NE |
| 7 | >512 | 1:80 | 256 | 1:160 | Additivity |
| 8 | >512 | 1:80 | 256 | 1:160 | Additivity |
| 9 | >512 | 1:160 | >512 | 1:160 | NE |
| 10 | 512 | 1:160 | 256 | 1:320 | Additivity |

*When synergy was not observed, the MIC for the combination was selected based on the nitrofurantoin MIC that provided the FIC value closest to 0.5. In the case where FIC values were the same, the MIC for the combination was based on the lowest nitrofurantoin MIC.
‡"NE" = No effect b. *Serratia marcescens*

Pre-test MIC ranged from 64–512 µg/ml for nitrofurantoin and dilution of 1:40 to 1:80 for uva ursi extract. In the presence of uva ursi, nitrofurantoin MIC ranged from 4–64 µg/ml. With uva ursi and nitrofurantoin combinations, four out of ten isolates demonstrated synergy, one additivity, and five had FIC values between synergy and additivity. Regardless of FIC calculations for synergy, the uva ursi and nitrofurantoin combination was at least 8-fold more active than nitrofurantoin by itself. Only one isolate demonstrated less than 4-fold increased activity in the presence of the uva ursi.

TABLE 1-3

Pre-test MIC of nitrofurantoin and *uva ursi* among *S. marcescens*

| Isolate ID | MIC (µg/ml) Nitrofurantoin | Dilution ratio *uva ursi* |
| --- | --- | --- |
| 11 | 256 | 1:80 |
| 12 | 256 | 1:40 |
| 13 | 512 | 1:80 |
| 14 | 256 | 1:40 |
| 15 | 256 | 1:40 |
| 16 | 64 | 1:80 |
| 17 | 256 | 1:40 |
| 18 | 256 | 1:40 |

TABLE 1-3-continued

Pre-test MIC of nitrofurantoin and *uva ursi* among *S. marcescens*

| Isolate ID | MIC (µg/ml) Nitrofurantoin | Dilution ratio *uva ursi* |
| --- | --- | --- |
| 19 | 256 | 1:80 |
| 20 | 256 | 1:80 |

TABLE 1-4

Test results for *S. marcescens* showing lowest fractional inhibitory concentration

| Isolate ID | MIC (µg/ml) Nitrofuran-toin | Dilution ratio *uva ursi* | MIC for combina-tion* | *Uva ursi* Dilution ratio at MIC | Result |
| --- | --- | --- | --- | --- | --- |
| 11 | 256 | 1:80 | 32 | 1:160 | 0.63 |
| 12 | 128 | 1:40 | 16 | 1:80 | 0.63 |
| 13 | 256 | 1:80 | 64 | 1:160 | 0.75 |
| 14 | 256 | 1:40 | 8 | 1:80 | Synergy |
| 15 | 256 | 1:40 | 4 | 1:80 | Synergy |
| 16 | 64 | 1:320 | 32 | 1:640 | Additivity |
| 17 | 256 | 1:40 | 64 | 1:160 | Synergy |
| 18 | 256 | 1:80 | 64 | 1:160 | 0.75 |
| 19 | 256 | 1:80 | 32 | 1:160 | 0.63 |
| 20 | 256 | 1:80 | 64 | 1:320 | Synergy |

*When synergy was not observed, the MIC for the combination was selected based on the nitrofurantoin MIC that provided the FIC value closest to 0.5. In the case where FIC values were the same, the MIC for the combination was based on the lowest nitrofurantoin MIC.

c. *Enterococcus faecalis*

Pre-test MIC ranged from 8–64 µg/ml for nitrofurantoin and dilutions of 1:160 to 1:5120 for uva ursi. In the presence of uva ursi. nitrofurantoin MIC ranged from 4–16 µg/ml. With the uva ursi and nitrofurantoin combinations, one out of ten isolates showed additivity, and nine demonstrated no change.

TABLE 1-5

Pre-test MIC of nitrofurantoin and *uva ursi* among *E. faecalis*

| Isolate ID | MIC (µg/ml) Nitrofurantoin | Dilution ratio *uva ursi* |
| --- | --- | --- |
| 21 | 64 | 1:280 |
| 22 | 16 | 1:640 |
| 23 | 16 | 1:160 |
| 24 | 8 | 1:1280 |
| 25 | 16 | 1:320 |
| 26 | 32 | 1:1280 |
| 27 | 8 | 1:320 |
| 28 | 32 | 1:1280 |
| 29 | 16 | 1:2560 |
| 30 | 8 | 1:5120 |

TABLE 1-6

Test results for *E. faecalis* showing lowest fractional inhibitory concentration

| Isolate ID | MIC (µg/ml) Nitrofuran-toin | Dilution ratio *uva ursi* | MIC for combina-tion | *Uva ursi* Dilution ratio at MIC | Result |
| --- | --- | --- | --- | --- | --- |
| 21 | 16 | 1:640 | 8 | 1:1280 | Additivity |
| 22 | 16 | 1:320 | 16 | 1:320 | NE‡ |
| 23 | 16 | 1:80 | 4 | 1:160 | 0.75 |
| 24 | 16 | >1:320 | 16 | >1:320 | NE |
| 25 | 16 | 1:160 | 16 | 1:160 | NE |
| 26 | 16 | 1:320 | 8 | 1:1280 | 0.75 |

TABLE 1-6-continued

Test results for *E. faecalis* showing lowest fractional inhibitory concentration

| Isolate ID | MIC (μg/ml) Nitrofurantoin | Dilution ratio uva ursi | MIC for combination | Uva ursi Dilution ratio at MIC | Result |
|---|---|---|---|---|---|
| 27 | 16 | 1:160 | 16 | 1:160 | NE |
| 28 | 16 | 1:1280 | 16 | 1:1280 | NE |
| 29 | 16 | 1:1280 | 16 | 1:1280 | NE |
| 30 | 8 | 1:2560 | 8 | 1:2560 | NE |

*When synergy was not observed the MIC for the combination was selected based on the nitrofurantoin MIC that provided the FIC value closest to 0.5. In the case where FIC values were the same, the MIC for the combination was based on the lowest nitrofurantoin MIC.
‡"NE" = No effect d. *Klebsiella pneumoniae*

Pre-test MICs ranged form 4 to >512 μg/ml for nitrofurantoin and dilutions of 1:40 to 1:80 for the uva ursi. In the presence of uva ursi, nitrofurantoin MICs ranged from 2–256 μg/ml. With the uva ursi and nitrofurantoin combinations, five out of ten isolates demonstrated additivity, one showed no effect and four had FIC values between synergy and additivity. Regardless of FIC calculation for synergy, the uva ursi and nitrofurantoin combination was at least 2-fold more active than nitrofurantoin by itself, in nine out of ten isolates tested.

TABLE 1-7

Pre test MIC of nitrofurantoin and *uva ursi* among *K. pneumoniae*

| Isolate ID | MIC (μg/ml) Nitrofurantoin | Dilution ratio uva ursi |
|---|---|---|
| 31 | 128 | 1:40 |
| 32 | 4 | 1:40 |
| 33 | 32 | 1:40 |
| 34 | 32 | 1:40 |
| 35 | 32 | 1:40 |
| 36 | 64 | 1:40 |
| 37 | 64 | 1:40 |
| 38 | 32 | 1:80 |
| 39 | >512 | 1:40 |
| 40 | 128 | 1:40 |

TABLE 1-8

Test results for *K. pneumoniae* showing lowest fractional inhibitory concentration

| Isolate ID | MIC (μg/ml) Nitrofuran-toin | Dilution ratio uva ursi | MIC for combina-tion* | Uva ursi Dilution ratio at MIC | Result |
|---|---|---|---|---|---|
| 31 | 256 | 1:40 | 256 | 1:40 | NE‡ |
| 32 | 4 | 1:40 | 2 | 1:80 | Additivity |
| 33 | 64 | 1:40 | 16 | 1:80 | 0.75 |
| 34 | 32 | 1:40 | 16 | 1:80 | Additivity |
| 35 | 32 | 1:40 | 16 | 1:80 | Additivity |
| 36 | 64 | 1:40 | 16 | 1:80 | 0.75 |
| 37 | 64 | 1:40 | 16 | 1:80 | 0.75 |
| 38 | 32 | 1:160 | 16 | 1:320 | Additivity |
| 39 | >512 | 1:40 | 128 | 1:80 | 0.75 |
| 40 | 128 | 1:40 | 64 | 1:80 | Additivity |

*When synergy was not observed, the MIC for the combination was selected based on the nitrofurantoin MIC that provided the FIC value closest to 0.5. In the case where FIC values were the same, the MIC for the combination was based on the lowest nitrofurantoin MIC.
‡"NE" = No effect e. *Proteus mirabilis.*

Pre-test MIC ranged from 16 to >512 μg/ml for nitrofurantoin and dilutions of 1:40 to 1:320 for the uva ursi. In the presence of uva ursi, nitrofurantoin MIC ranged from 2–128 μg/ml. With the uva ursi and nitrofurantoin combinations, four out of ten isolates demonstrated synergy. The remaining six isolates had FIC values between synergy and additivity. Regardless of FIC calculations for synergy, the uva ursi and nitrofurantoin combination was two to seven dilutions more active than nitrofurantoin by itself.

TABLE 1-9

Pre test MIC of nitrofurantoin and *uva ursi* among *P. mirabilis*

| Isolate ID | MIC (μg/ml) Nitrofurantoin | Dilution ratio uva ursi |
|---|---|---|
| 41 | 128 | 1:160 |
| 42 | 16 | 1:160 |
| 43 | 256 | 1:160 |
| 44 | >512 | 1:160 |
| 45 | 32 | 1:320 |
| 46 | 256 | 1:320 |
| 47 | 256 | 1:160 |
| 48 | 128 | 1:320 |
| 49 | 256 | 1:40 |
| 50 | 128 | 1:160 |

TABLE 1-10

Test results for *P. mirabilis* showing lowest fractional inhibitory concentration

| Isolate ID | MIC (μg/ml) Nitrofuran-toin | Dilution ratio uva ursi extract | MIC for combina-tion* | Uva ursi Dilution ratio at MIC | Result |
|---|---|---|---|---|---|
| 41 | 128 | 1:160 | 32 | 1:640 | Synergy |
| 42 | 26 | 1:320 | 4 | 1:640 | 0.75 |
| 43 | 256 | 1:160 | 32 | 1:640 | Synergy |
| 44 | >512 | 1:160 | 64 | 1:320 | 0.63 |
| 45 | 32 | 1:160 | 8 | 1:640 | Synergy |
| 46 | 256 | 1:320 | 128 | 1:2560 | 0.63 |
| 47 | 256 | 1:160 | 64 | 1:640 | Synergy |
| 48 | 128 | 1:320 | 32 | 1:640 | 0.75 |
| 49 | 128 | 1:160 | 8 | 1:320 | 0.56 |
| 50 | 128 | 1:160 | 2 | 1:320 | 0.52 |

*When synergy was not observed, the MIC for the combination was selected based on the nitrofurantoin MIC that provided the FIC value closest to 0.5. In the case where FIC values were the same, the MIC for the combination was based on the lowest nitrofurantoin MIC.

f. *Escherichia coli*

Pre-test MIC ranged from 32 to >512 μg/ml for nitrofurantoin and dilutions of 1:40 to 1:80 for the uva ursi. In the presence of uva ursi, nitrofurantoin MIC ranged from 4–128 μg/ml. With the uva ursi and nitrofurantoin combinations, six out of ten isolates demonstrated synergy. The remaining four isolates had FIC values between synergy and additivity. Regardless of FIC calculations for synergy, the uva ursi and nitrofurantoin combination was one to six dilutions more than nitrofurantoin by itself, with six isolates at least 4 dilutions more active than nitrofurantoin by itself.

TABLE 1-11

Pre-test MICs of nitrofurantoin and *uva ursi* among *E. coli*

| Isolate ID | MIC (μg/ml) Nitrofurantoin | Dilution ratio uva ursi |
|---|---|---|
| 51 | >512 | 1:80 |
| 52 | >512 | 1:80 |
| 53 | >512 | 1:40 |
| 54 | 32 | 1:40 |
| 55 | 256 | 1:80 |
| 56 | 128 | 1:80 |

TABLE 1-11-continued

Pre-test MICs of nitrofurantoin and *uva ursi* among *E. coli*

| Isolate ID | MIC (μg/ml) Nitrofurantoin | Dilution ratio *uva ursi* |
|---|---|---|
| 57 | 64 | 1:40 |
| 58 | 128 | 1:40 |
| 59 | >512 | 1:80 |
| 60 | 64 | 1:40 |

TABLE 1-12

Test results for *E. coli* showing lowest fractional inhibitory concentration

| Isolate ID | MIC (μg/ml) Nitrofurantoin | Dilution ratio *uva ursi* | MIC for combination* | *Uva ursi* Dilution ratio at MIC | Result |
|---|---|---|---|---|---|
| 51 | >512 | 1:80 | 128 | 1:320 | Synergy |
| 52 | >512 | 1:80 | 32 | 1:160 | 0.56 |
| 53 | 32 | 1:40 | 4 | 1:80 | 0.63 |
| 54 | 32 | 1:40 | 8 | 1:160 | Synergy |
| 55 | 128 | 1:160 | 64 | 1:640 | 0.75 |
| 56 | 64 | 1:40 | 16 | 1:160 | Synergy |
| 57 | 64 | 1:40 | 16 | 1:160 | Synergy |
| 58 | 128 | 1:80 | 64 | 1:640 | 0.63 |
| 59 | >5122 | 1:80 | 128 | 1:320 | Synergy |
| 60 | 64 | 1:40 | 16 | 1:320 | Synergy |

*When synergy was not observed, the MIC for the combination was selected based on the nitrofurantoin MIC that provided the FIC value closest to 0.5. In the case where FIC values were the same the MIC for the combination was based on the lowest nitrofurantoin MIC.

g. *Staphylococcus saprophyticus*

Pre-test MIC ranged from 8 to 32 μg/ml for nitrofurantoin and dilutions of 1:160 to 1:1280 for the uva ursi. In the presence of uva ursi, nitrofurantoin MIC ranged from 5–8 μg/ml. With the uva ursi and nitrofurantoin combinations, three out of ten isolates demonstrated synergy. The remaining seven isolates had MIC values between synergy and additivity. Regardless of FIC calculations for synergy, the uva ursi and nitrofurantoin combination was one to four dilutions more than nitrofurantoin by itself.

TABLE 1-13

Pre-test MIC of nitrofurantoin and *uva ursi* among *S. saprophyticus*

| Isolate ID | MIC (μg/ml) Nitrofurantoin | Dilution ratio *uva ursi* |
|---|---|---|
| 61 | 16 | 1:320 |
| 62 | 16 | 1:320 |
| 63 | 16 | 1:320 |
| 64 | 32 | 1:320 |
| 65 | 16 | 1:160 |
| 66 | 16 | 1:320 |
| 67 | 16 | 1:320 |
| 68 | 16 | 1:320 |
| 69 | 8 | 1:1280 |
| 70 | 16 | 1:320 |

TABLE 1-14

Test results for *S. saprophyticus* showing lowest fractional inhibitory concentration

| Isolate ID | MIC (μg/ml) Nitrofurantoin | Dilution ratio *uva ursi* extract | MIC for combination* | *Uva ursi* Dilution ratio at MIC | Result |
|---|---|---|---|---|---|
| 61 | 16 | 1:320 | 8 | 1:5120 | 0.56 |
| 62 | 32 | 1:160 | 4 | 1:320 | 0.63 |
| 63 | 16 | 1:320 | 6 | 1:5120 | 0.56 |
| 64 | 8 | 1:160 | 1 | 1:320 | 0.56 |
| 65 | 16 | 1:320 | 8 | 1:640 | Additivity |
| 66 | 16 | 1:320 | 8 | 1:5120 | 0.56 |
| 67 | 16 | 1:160 | 2 | 1:320 | 0.63 |
| 68 | 16 | 1:320 | 8 | 1:640 | Additivity |
| 69 | 8 | 1:1280 | 0.5 | 1:2560 | 0.56 |
| 70 | 16 | 1:320 | 8 | 1:640 | Additivity |

*When synergy was not observed, the MIC for the combination was selected based on the nitrofurantoin MIC that provided the FIC value closest to 0.5. In the case where FIC values were the same, the MIC for the combination was based on the lowest nitrofurantoin MIC.

D. Summary of Results

The combination of nitrofurantoin with uva ursi was capable of reducing the MIC of nitrofurantoin against nearly all the isolates tested. When synergy was defined as Fractional Inhibitory Concentration (FIC) value of =0.5, nitrofurantoin and uva ursi were synergistic against strains of four of the seven species tested.

TABLE 2.1

Organisms by which synergy of combination is demonstrated

| Organism | No. of strains where nitrofurantoin in combination with *uva ursi* was synergistic (FIC = 0.5) |
|---|---|
| *Escherichia coli* | 6/10 |
| *Serratia marcescens* | 4/10 |
| *Proteus mirabilis* | 4/10 |
| *Pseudomonas aeruginosa* | 1/10 |

The four strains of *E. coli* that did not demonstrate synergy had FIC values ranging from 0.56 to 0.75 (between synergy and additivity).

The activity of nitrofurantoin against all strains of *S. marcescens* was enhanced in the presence of uva ursi. Four strains had FIC =0.5, and six strains had FIC ranging from 0.63 to 1.

Nitrofurantoin and uva ursi were synergistic against four strains of *P. mirabilis*. In addition, the MIC of nitrofurantoin for one strain was reduced from 128 μg/ml to 2 μg/ml. Although this was a six doubling dilution decrease in MIC, the FIC was 0.52, which is between synergy and additivity.

Nitrofurantoin in combination with uva ursi was synergistic against one strain of *P. aeruginosa* (MIC reduction from >512 μg/ml to 0.25 μg/ml in the presence of a 1/80 dilution of uva ursi). Four strains had FIC of 1, demonstrating additivity. Uva ursi had no effect on the antimicrobial activity of the remaining five strains.

Although none of the drug combinations were synergistic against any of the *K. pneumoniae* isolates tested, the FIC values of four strains were 0.75. Uva ursi had no effect on the activity of nitrofurantoin against one strain and showed additivity for the remaining five strains.

In the case of *S. saprophyticus*, none of the strains gave FIC =0.5. However, for all organisms the MIC for nitrofurantoin was reduced in the presence of uva ursi. For example, the MIC of one strain was reduced from 8 µg/ml to 0.5 µg/ml in the presence of 1/2,560 dilution of uva ursi (FIC =0.56).

E. faecalis was the least susceptible organism to the nitrofurantoin and uva ursi combinations. None of the strains displayed synergy based on FIC values. Two strains resulted in FIC values between synergy and additivity (0.75), and one strain demonstrated additivity. Uva ursi had no effect on the activity of nitrofurantoin against the remaining seven strains tested.

In sum, uva ursi enhanced antimicrobial activity against a wide variety of strains tested. In several cases, the drug combinations were synergistic, with FIC values of =0.5. There were also many cases where the activity of nitrofurantoin was enhanced in the presence of uva ursi, with FIC values ranging from >0.5 to 1 (between synergy and additivity). The extent of synergy was organism-dependent, with E. coli the most susceptible and E. faecalis the least susceptible.

VII. Example—Compositions and Methods of Use

All references described herein are hereby incorporated by reference.

All percentages, ratios and proportions herein are by weight, unless otherwise specified.

The compositions and kits of the present invention are useful in the prevention and treatment of infectious disorders. The following composition and kit examples do not limit the invention. The skilled practitioner will appreciate that the examples and may be varied based on the condition being treated and the patient.

Example I.

A tablet form of the present invention is made by combining the following components using conventional mixing and tableting technology.

| Component | % (by weight) |
| --- | --- |
| Uva ursi lyophilized extract | 17.6 |
| Nitrofurantoin monohydrate | 49.4 |
| Ethylcellulose, 100 cps (5% ethanol soln) | 10 |
| Starch | 16 |
| Talc | 6 |
| Stearic Acid | 1 |

The uva ursi lyophilized extract and nitrofurantoin monohydrate are granulated with 5% ethylcellulose in ethanol. The granules are then passed through a 12-mesh screen and dried at 120° F. To the dried granulation is added starch acid. The granulation mixture is passed through a 20 mesh screen. To the sieved granulation is added the starch and talc with mixing until uniform. The resultant granulation mixture is then compressed using conventional tableting processes. The resulting tablets are 250 mg.

A human subject suffering from a urinary tract infection is administered approximately 1,000 mg of these tablets, 2 times a day, for 10 days in a typical treatment regimen.

Example II.

A composition according to the present invention is made comprised as follows:

| Component | % (by weight) |
| --- | --- |
| Nitrofuratoin particulates* | 1 |
| Nitrofuratoin monohydrate | 0.025 |
| Magnesium aluminum silicate | 0.50 |
| Uva ursi‡ fluid extract (40% ethanol) | 0.05 |
| Xanthan gum | 0.60 |
| Flavorants | 0.08 |
| Methyl paraben | 0.12 |
| Propyl parben | 0.02 |
| Purified water | 97.605 |

*Made according to the method described in Example I of U.S. Pat. No. 5,178,880.
‡Comprised of Arctostaphylos uva-ursi.

The composition is made by dissolving the methyl paraben, propyl paraben, and flavorant in a portion of the water, followed by the magnesium aluminum silicate, to form a "bulk mixture". The bulk mixture is then stirred for approximately 1 hour. The xanthan gum is then added to the bulk mixture, and stirred for approximately 20 minutes. The nitrofurantoin particulates and uva ursi fluid extract are then added, and the final composition is stirred for approximately 1 hour.

A human subject suffering from acute cystitis is administered approximately 20 ml of this suspension, 4 times a day, for 10 days in a typical treatment regimen.

Example III

A composition according the present invention is made according to Example II but an equivalent amount of amount of uva ursi comprising a 1:1:1 mixture of Arctostaphylos adenotricha, Arctostaphylos coactylis, and Arctostaphylos uva-ursi is used instead of uva ursi comprising Arctostaphylos uva-ursi alone.

Example IV.

A kit for treating an infectious disorder according to the present invention is packaged in a single-source container, as follows:

Kit

Macrodantin® tablets at 200 mg
Bearberry leaf tablets at 700 mg
Instructions for use A human subject suffering from a gastrointestinal tract infection, per the instructions of the kit, is administered one (1) tablet of Macrodantin® and Bearberry leaf respectively, three times a day, for 7 days. The infection is thereby eradicated.

While particular embodiments of the present invention have been described, it will be apparent to those skilled in the art that Various changes and modifications of the present invention can be made without departing from the spirit and scope of the invention. It is intended to cover, in the appended claims, all such modifications that are within the scope of the present invention.

What is claimed is:

1. A method of treating an infectious disorder, the method comprising administering nitrofurantoin at least once daily for a period of at least 1 day and concurrently administering uva ursi at least once daily for a period of at least 1 day to a subject in need thereof.

2. The method of claim 1 wherein the uva ursi is selected from the group consisting of *Arctostaphylos adenotricha, Arctostaphylos coactylis* and *Arctostaphylos uva-ursi*.

3. The method of claim 2 wherein the uva ursi is *Arctostaphylos uva-ursi*.

4. The method of claim 1 wherein the nitrofurantoin and uva ursi are administered via a unit dose form.

5. The method of claim 4 wherein the nitrofurantoin and uva ursi are each administered via a combined unit dose.

6. The method of claim 4 wherein the nitrofurantoin and uva ursi are administered via separate unit doses.

7. The method of claim 1 wherein the nitrofurantoin is administered 1–4 times daily, and the uva ursi is concurrently administered 1–4 times daily for at least 2 days.

8. The method of claim 1 wherein the infectious disorder is selected from the group consisting of urinary tract infections, cystitis and pyelonephritis.

9. A method according to claim 1 wherein the infections disorder is an upper-gastrointestinal disorder mediated by *Campylobacter pylori*.

10. A method according to claim 9 wherein the disorder is an ulcer.

11. A method of treating an infectious disorder comprising administering a kit, wherein the kit comprises: (a) nitrofurantoin in a unit dose form; (b) uva ursi in unit dose form; and (c) a package containing components (a) and (b).

12. The method of claim 11, wherein the uva ursi is selected from the group consisting of *Arctostaphylos adenotricha, Arctostaphylos coactylis* and *Arctostaphylos uva-ursi*.

13. The method of claim 12, wherein the uva ursi is *Arctostaphylos uva-ursi*.

14. The method of claim 11, wherein the nitrofurantoin and uva ursi are administered via a unit dose form.

15. The method of claim 14, wherein the nitrofurantoin and uva ursi are each administered via a combined unit dose.

16. The method of claim 14, wherein the nitrofurantoin and uva ursi are administered via separate unit doses.

17. The method of claim 11, wherein the nitrofurantoin unit dose form is administered 1–4 times daily; and the uva ursi unit dose form is concurrently administered 1–4 times daily for at least 2 days.

18. The method of claim 11, wherein the infectious disorder is selected from the group consisting of urinary tract infections, cystitis and pyelonephritis.

19. The method according to claim 11, wherein the infections disorder is an upper-gastrointestinal disorder mediated by *Campylobacter pylori*.

20. The method according to claim 19, wherein the disorder is an ulcer.

* * * * *